(12) United States Patent
Moor et al.

(10) Patent No.: US 10,064,374 B2
(45) Date of Patent: *Sep. 4, 2018

(54) DOWNY MILDEW RESISTANT LETTUCE

(75) Inventors: Cornelis Marinus Moor, Monster (NL); Egbert Carolus Johannes Smits, Zevenbergen (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 0 days.

This patent is subject to a terminal disclaimer.

(21) Appl. No.: 12/852,860

(22) Filed: Aug. 9, 2010

(65) Prior Publication Data

US 2010/0306872 A1 Dec. 2, 2010

Related U.S. Application Data

(62) Division of application No. 11/484,363, filed on Jul. 11, 2006, now Pat. No. 7,790,962.

(60) Provisional application No. 60/698,109, filed on Jul. 11, 2005.

(51) Int. Cl.
*A01H 5/12* (2018.01)
*A01H 6/14* (2018.01)

(52) U.S. Cl.
CPC ............. *A01H 5/12* (2013.01); *A01H 6/1472* (2018.05)

(58) Field of Classification Search
None
See application file for complete search history.

(56) References Cited

U.S. PATENT DOCUMENTS

| | | | |
|---|---|---|---|
| 6,320,104 B1 * | 11/2001 | Moor et al. | 800/305 |
| 6,555,735 B2 * | 4/2003 | Sarreal | 800/305 |
| 6,689,941 B2 | 2/2004 | Waycott | |
| 6,903,249 B2 * | 6/2005 | Lambalk et al. | 800/305 |
| 7,790,962 B2 * | 9/2010 | Moor et al. | 800/305 |
| 8,772,579 B2 * | 7/2014 | Moor et al. | 800/305 |

OTHER PUBLICATIONS

Lebeda and Zinkernagel 2003, Plant Pathology 52: 41-51.*
Van Ettekoven, K. et al., "Identification and denomination of 'new' races of *Bremia lactllcae*"In: Lebeda, A. and Kristkova, E (eds.), Eucarpia Leafy Vegetables, Palacky University, Olomouc, Czech Republic, pp. 171-175, 1999.
Bonnier, F.J.M. et al.,"New sources of major gene resistance in *Lactllca* to *Bremia lactllcae*"Euplivtica, 61(3), pp. 203-211,1992.
Lebeda, A. et al., "Race-specific resistance genes to *Bremia lactllcae* Regal in new Czechoslovak lettuce cultivars and location of resistance in a *Lactllca serriola* X *Lacllica sativa* hybrid" Archivelfur-Phytopathologie-und-pl flanzenschutz, 27(1), pp. 65-72, 1991.
Mendel G., "Experiments in Plant Hybridization (1865)" Versuche tiber Pflanzen-Hybriden. Verhandlungen des naturforschenden Vereines in Brunn, 4, pp. 3-39, (Abh.) 1865.
Dede, Y., "Development of the Downy Mildew Pathogen *Bremia Lactllcae* on Transgenic Lettuce Expressing a Bacteria 3-1,3-Glucanase" Tr. J. of Agriculture and Forestry, 22, pp. 313-321, 1998.

* cited by examiner

*Primary Examiner* — David H Kruse
(74) *Attorney, Agent, or Firm* — Duane Morris LLP; Thomas J. Kowalski; Deborah L. Lu

(57) ABSTRACT

The present invention relates to a lettuce cultivar having resistance to downy mildew (*Bremia lactucae*) and which has an extraordinary high number of green, round-shaped leaves. The invention further relates to methods for producing the lettuce cultivar, represented by lettuce variety 79-22 RZ, referred to as Socrates, representative seed having been deposited under NCIMB Accession No. 41325.

16 Claims, 1 Drawing Sheet

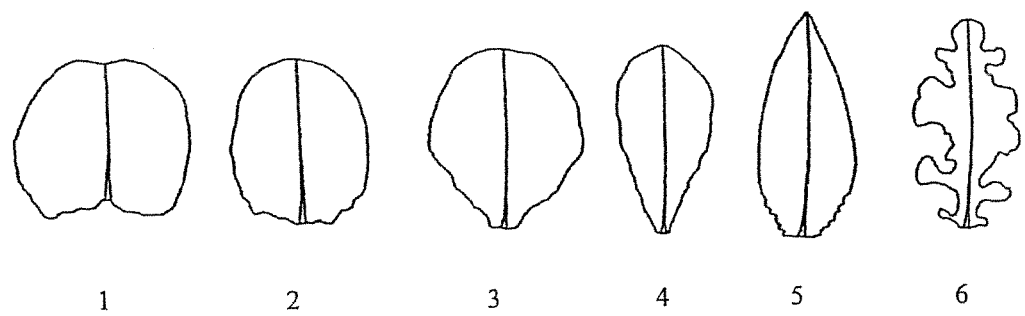
Fig. 1. Six different shapes of the fourth leaf from a 20-day old seedling grown under optimal conditions.

DOWNY MILDEW RESISTANT LETTUCE

CROSS REFERENCE TO RELATED APPLICATION

The present application is a divisional of U.S. application Ser. No. 11/484,363, filed Jul. 11, 2006 and issued as U.S. Pat. No. 7,790,962 on Sep. 7, 2010, which claims benefit of U.S. Provisional Application No. 60/698,109, filed Jul. 11, 2005, which is incorporated by reference in its entirety herein.

BACKGROUND OF THE INVENTION

Field of the Invention

The present invention relates to a new lettuce (*Lactuca sativa*) variety which exhibits resistance against downy mildew (*Bremia lactucae*).

Description of Related Art

All cultivated forms of lettuce belong to the highly polymorphic species *Lactuca sativa* that is grown for its edible head and leaves. As a crop, lettuces are grown commercially wherever environmental conditions permit the production of an economically viable yield.

*Lactuca sativa* is in the Cichoreae tribe of the Asteraceae (Compositae) family. Lettuce is related to chicory, sunflower, aster, dandelion, artichoke and chrysanthemum. *Sativa* is one of about 300 species in the genus *Lactuca*.

Lettuce cultivars are susceptible to a number of diseases such as downy mildew, sclerotinia rot, botrytis, powdery mildew, anthracnose, bottom rot, corky root rot, lettuce mosaic virus, big vein, beet western yellows and aster yellows. These diseases result in millions of dollars of lost lettuce crop throughout the world every year.

Of the various diseases that affect lettuce cultivars, downy mildew (*Bremia lactucae*) is the most highly destructive of lettuce grown at relatively low temperature and high humidity. Downy mildew is caused by a fungus, *Bremia lactucae* Regal, which can be one of the following strains: NL1, NL2, NL4, NL5, NL6, NL7, NL10, NL12, NL13, NL14, NL15, NL16, B1:17, B1:21 and B1:23 (Van Ettekoven, K. et al., "Identification and denomination of 'new' races of *Bremia lactucae*." In: Lebeda, A. and Kristkova, E (eds.), Eucarpia Leafy Vegetables, 1999, Palacky University, Olomouc, Czech Republic, pp. 171-175).

Downy mildew causes pale, angular, yellow areas bounded by veins on the upper leaf surfaces. Sporulation occurs on the opposite surface of the leaves. The lesions eventually turn brown, and they may enlarge and coalesce. These symptoms typically occur first on the lower leaves of the lettuce, but under ideal conditions may move into the upper leaves of the head. When the fungus progresses to this degree, the head cannot be harvested. Less severe damage requires the removal of more leaves than usual, especially when the lettuce reaches its final destination.

Although several known lettuce cultivars exhibit resistance against downy mildew, irrespective of lettuce type, all the lettuce cultivars affected produce a limited number of leaves that generally are of unequal size and diminished quality with respect to color and shape. This is a distinct disadvantage for processing purposes because leaves either need to be sorted based on size or they need to be cut to a smaller, more uniform size. The first option requires additional labor, with not all sizes usable. The second option has the disadvantage that it creates many cut surfaces which then are subject to wound-induced browning, resulting in a greatly reduced shelf-life.

A need exists, therefore, for an improved lettuce variety which exhibits resistance to downy mildew and exhibits abundant leaf growth and vibrant color.

SUMMARY OF THE INVENTION

The present invention provides a new type of lettuce (*Lactuca sativa*) variety, designated 79-22 RZ and referred to as Socrates. Lettuce cultivar 79-22 RZ exhibits a combination of resistance to downy mildew (*Bremia lactucae* Regal) as well as an extraordinary high number of uniformly sized, green, round-shaped leaves. Seeds of lettuce cultivar 79-22 RZ have been deposited with the National Collections of Industrial, Marine and Food Bacteria (NCIMB) in Bucksburn, Aberdeen AB21 9YA, Scotland, UK and have been assigned NCIMB Accession No. 41325.

The present invention also provides parts of the plant of lettuce cultivar 79-22 RZ that are suitable for sexual reproduction, which include, without limitation, microspores, pollen, ovaries, ovules, embryo sacs or egg cells.

The present invention further provides parts of the plant of lettuce cultivar 79-22 RZ that are suitable for vegetative reproduction, which include, without limitation, cuttings, roots, stems, cells or protoplasts, leaves, meristems or buds.

The present invention still further provides a tissue culture from lettuce cultivar 79-22 RZ in which the tissue culture is derived from a tissue such as, for example and without limitation, leaves, pollen, embryos, cotyledon, hypocotyls, meristematic cells, roots, root tips, anthers, flowers, seeds or stems.

The present invention also provides a plant grown from the seeds, regenerated from the above-described plant parts, or regenerated from the above-described tissue culture, having all of the morphological and physiological characteristics of lettuce cultivar 79-22 RZ.

The present invention further provides progeny of lettuce cultivar 79-22 RZ produced by sexual or vegetative reproduction, grown from seeds, regenerated from the above-described plant parts, or regenerated from the above-described tissue culture of the lettuce cultivar or a progeny plant thereof, in which the regenerated plant has all of the morphological and physiological characteristics of lettuce cultivar 79-22 RZ.

The present invention still further provides a method of producing a hybrid lettuce seed comprised of crossing a first parent lettuce plant with a second parent lettuce plant and harvesting the resultant hybrid lettuce seed, in which the first parent lettuce plant or the second parent lettuce plant is the lettuce cultivar 79-22 RZ.

The present invention also provides a method of producing a lettuce cultivar having resistance to downy mildew (*Bremia lactucae* Regal) as well as an extraordinary high number of green, round-shaped leaves, comprised of crossing a mother lettuce plant, such as, for example and without limitation, a mother plant of the indoor butterhead lettuce variety, with a father lettuce plant, such as, for example and without limitation, a father plant of a BC-5 product of a backcross program to introduce the CS-RL *Bremia* resistance factor.

DEPOSIT

The Deposits with National Collections of Industrial, Marine and Food Bacteria (NCIMB) in Bucksburn, Aberdeen AB21 9YA, Scotland, UK, under deposit accession number 41325 were made pursuant to the terms of the Budapest Treaty. Upon issuance of a patent, all restrictions upon the deposit will be removed, and the deposit is intended to meet the requirements of 37 CFR § § 1.801-1.809. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

FIG. 1 is an illustration of six different shapes of the fourth leaf from a 20-day old seedling grown under optimal conditions.

DETAILED DESCRIPTION OF THE INVENTION

The present invention provides a new type of lettuce (*Lactuca sativa*) variety, designated 79-22 RZ and referred to as Socrates. Lettuce cultivar 79-22 RZ exhibits a combination of resistance to downy mildew (*Bremia lactucae* Regal) as well as an extraordinary high number of uniformly sized, green, round-shaped leaves. Seeds of lettuce cultivar 79-22 RZ have been deposited with the National Collections of Industrial, Marine and Food Bacteria (NCIMB) in Bucksburn, Aberdeen AB21 9YA, Scotland, UK and have been assigned NCIMB Accession No. 41325.

As used herein, resistance to *Bremia lactucae* Regal is defined as the capacity of a plant to resist infection by each of the aforementioned strains of the *Bremia lactucae* Regal in all stages between the seedling stage and the harvestable plant stage.

Resistance typically is tested by two interchangeable methods, as described by Bonnier, F. J. M. et al. (Euphytica, 61(3):203-211, 1992). One method involves inoculating 7-day old seedlings and observing sporulation 10 to 14 days later. The other method involves inoculating leaf discs with a diameter of 18 mm obtained from a non-senescent, fully grown true leaf and observing sporulation 10 days later.

As used herein, an extraordinary high leaf number is the leaf number of a lettuce plant which is at least about two times to about four times as high as the leaf number of a plant of a regular lettuce variety grown in the same environment during the same period of time.

As used herein, an acceptable product for consumers and/or the lettuce processing industry is defined as the absence of tipburn, short core and an extraordinary high number of relatively uniform-sized, green, round-shaped lettuce leaves.

In an embodiment of the present invention, there also is provided parts of the plant of lettuce cultivar 79-22 RZ that are suitable for sexual reproduction, which include, without limitation, microspores, pollen, ovaries, ovules, embryo sacs or egg cells.

In another embodiment, there is provided parts of the plant of lettuce cultivar 79-22 RZ that are suitable for vegetative reproduction, which include, without limitation, cuttings, roots, stems, cells, protoplasts, leaves, meristems or buds.

In a further embodiment, there is provided a tissue culture from lettuce cultivar 79-22 RZ in which the tissue culture is derived from a tissue such as, for example and without limitation, leaves, pollen, embryos, cotyledon, hypocotyls, meristematic cells, roots, root tips, anthers, flowers, seeds or stems.

In still a further embodiment, there is provided a plant grown from the seeds, regenerated from the above-described plant parts, or regenerated from the above-described tissue culture, having all of the morphological and physiological characteristics of lettuce cultivar 79-22 RZ.

In still another embodiment, there is provided progeny of lettuce cultivar 79-22 RZ produced by sexual or vegetative reproduction, grown from seeds, regenerated from the above-described plant parts, or regenerated from the above-described tissue culture of the lettuce cultivar or a progeny plant thereof, in which the regenerated plant has all of the morphological and physiological characteristics of lettuce cultivar 79-22 RZ. Progeny of the lettuce cultivar 79-22 RZ can be modified in one or more other characteristics, in which the modification is a result of, for example and without limitation, mutagenesis or transformation with a transgene.

In still a further embodiment, there is provided a method of producing a hybrid lettuce seed comprised of crossing a first parent lettuce plant with a second parent lettuce plant and harvesting the resultant hybrid lettuce seed, in which the first parent lettuce plant or the second parent lettuce plant is the lettuce cultivar 79-22 RZ.

In still another embodiment, there is provided a method of producing a lettuce cultivar having resistance to downy mildew (*Bremia lactucae* Regal) as well as an extraordinary high number of green, round-shaped leaves, comprised of crossing a mother lettuce plant, such as for example and without limitation, a mother plant of the indoor butterhead lettuce variety, with a father lettuce plant, such as for example and without limitation, a father plant of a BC-5 product of a backcross program to introduce the CS-RL *Bremia* resistance factor.

In a preferred embodiment, the specific type of breeding method employed for developing a lettuce cultivar is pedigree selection, where both single plant selection and mass selection practices are employed. Pedigree selection, also known as the "Vilmorin system of selection," is described in Fehr, W., *Principles of Cultivar Development*, Volume I, MacMillan Publishing Co., which is hereby incorporated by reference.

In general, selection is first practiced among $F_2$ plants. In the next season, the most desirable $F_3$ lines are first identified, then desirable $F_3$ plants within each line are selected. The following season and in all subsequent generations of inbreeding, the most desirable families are identified first, then desirable lines within the selected families are chosen, and finally desirable plants within selected lines are harvested individually. A family refers to lines that were derived from plants selected from the same progeny from the preceding generation.

Using this pedigree method, two parents may be crossed using an emasculated female and a pollen donor (male) to produce $F_1$ offspring. Lettuce is an obligate self-pollination species, which means that pollen is shed before stigma emergence, assuring 100% self-fertilization. Therefore, in order to optimize crossing, a method of misting may be used to wash the pollen off prior to fertilization to assure crossing or hybridization.

Parental varieties are selected from commercial varieties that individually exhibit one or more desired phenotypes. Additionally, any breeding method involving selection of plants for the desired phenotype can be used in the method of the present invention.

The $F_1$ may be self-pollinated to produce a segregating $F_2$ generation. Individual plants may then be selected which represent the desired phenotype in each generation ($F_3$, $F_4$, $F_5$, etc.) until the traits are homozygous or fixed within a breeding population.

The characteristic of lettuce having an extraordinary high leaf number is caused by a single genetic factor, which is introduced via crossing with a multileaf plant and then selecting for the distinct group of descendants with a higher leaf number than the contrasting group of descendants with a lower leaf number (U.S. Pat. No. 6,320,104). These distinct groups easily can be recognized in an $F_2$-population from a single cross between a multileaf lettuce plant and a plant of a regular lettuce variety without an extraordinary high leaf number by a cumulative frequency distribution graph of leaf number per plant, which can be supported by statistical analysis based on mixture models.

Based on a likelihood ratio test, it can be shown that a bimodal distribution supports the observed distribution of plant leaf numbers much better than a unimodal distribution. The number of plants belonging to the two distinguishable groups, i.e., high leaf number and low leaf number, follows a typical Mendelian segregation ratio of 1:3, indicating a single recessive genetic factor for the high leaf number trait. The observation that the ratio between the two group sizes follows a 1:3 segregation ratio can be supported statistically by a chi-square test.

The present invention is more particularly described in the following non-limiting example, which is intended to be illustrative only, as numerous modifications and variations therein will be apparent to those skilled in the art.

Example 1

Development and Characteristics of Lettuce Cultivar 79-22 RZ

The breeding history of the lettuce cultivar of the present invention was as follows. In 1991, the breeding of "Socrates" began with a cross between the indoor butterhead lettuce variety "Gypsy" (Rijk Zwaan) as the mother plant with a BC-5 product of a backcross program as the father plant. The purpose of the BC-5 product backcross program was to introduce the CS-RL *Bremia* resistance factor into the recurrent parent "Miledie" (Rijk Zwaan), an indoor butterhead lettuce variety.

In 1992, an $F_3$-line descending from this cross was sown in an autumn glasshouse trial in Maasdijk, The Netherlands. In November, 1992, an $F_3$-plant was selected as being *Bremia*-resistant and accepted as a butterhead lettuce product for consumers. The $F_3$-plant was used as a father in a cross with a plant of the indoor butterhead lettuce variety "Rex" (Rijk Zwaan). The purpose of using the "Rex" variety was to introduce two characteristics: slow bolting and decreased tipburn sensitivity, thus making the descendants more suitable for indoor lettuce production under warm conditions.

In 1996, an $F_5$-line descending from this cross was sown in an autumn glasshouse trial in Monster, The Netherlands. In November, 1996, an $F_5$-plant, designated 97S.303, was selected as being *Bremia*-resistant and acceptable as a butterhead lettuce product for consumers. A seed, designated RZ97.41561, which provided plants with a multileaf characteristic, was sown in the same trial. A multileaf lettuce plant from this seed, designated 97S.307, was selected and used as a mother in a cross with the selected $F_5$-plant, designated 97S.303 as the father. In 1997, an $F_1$-plant resulting from this cross was grown in Hendrik-Ido-Ambacht, The Netherlands, to produce an $F_2$-seed, designated 98S.44293, which was sown in a spring glasshouse trial in 's-Gravenzande, The Netherlands.

In April, 1998, an $F_2$-plant was selected for having an extraordinary high leaf number and having *Bremia* resistance. The $F_2$-plant produced $F_3$-seed, designated 99S.42742, which was sown in a spring glasshouse trial in De Lier, The Netherlands. In April, 1999, it was observed in this trial that the $F_3$-seed produced plants with an extraordinary high leaf number, resulting in a harvestable product acceptable for consumers. At this time, an $F_3$-plant was selected from the trial as having an extraordinary high leaf number and having *Bremia* resistance. The $F_3$-plant produced $F_4$-seed, designated 00S.43218, which was sown in a spring glasshouse trial in 's-Gravenzande, The Netherlands. In April, 2000, it was observed in this trial that the $F_4$-seed produced plants with an extraordinary high leaf number, resulting in a harvestable product acceptable for consumers.

At this time, an $F_4$-plant was selected from the trial as having an extraordinary high leaf number and having *Bremia* resistance. The $F_4$-plant produced $F_5$-seed, designated 01S.43883, which was sown in an autumn glasshouse trial in De Lier, The Netherlands. In November, 2000, it was observed in this trial that the $F_5$-seed produced plants with an extraordinary high leaf number, resulting in a harvestable product acceptable for consumers. At this time, an $F_5$-plant was selected from the trial as having an extraordinary high leaf number and having *Bremia* resistance. The $F_5$-plant produced $F_6$-seed, designated 01S.44311, of which one seed was sown in a greenhouse trial in Fijnaart, The Netherlands, to produce an $F_6$ plant. The only selection criterion applied for this generation was *Bremia* resistance.

In 2001, the $F_6$-plant produced $F_7$-seed, designated 02S.22783, which was uniformly resistant against downy mildew (*Bremia lactucae*). Based on several trials performed in 2001 and 2002, the $F_7$-seed also was uniform for type, field performance, bolting and sensitivity for tipburn.

In the spring of 2002, the $F_7$-seed was used to sow a multiplication in 's-Gravenzande, The Netherlands. The progeny of this multiplication showed phenotypical uniformity during seed production and seed was harvested for further trials in 2003. In several confidential trials conducted in 2003, the multiplied seed, designated by the introduction number 79-22 RZ, displayed a harvested product which had the characteristics acceptable by the lettuce processing industry and/or consumers. Seeds of 79-22 RZ, referred to as "Socrates", have been deposited with the National Collections of Industrial, Marine and Food Bacteria (NCIMB) in Bucksburn, Aberdeen AB21 9YA, Scotland, UK and have been assigned NCIMB Accession No. 41325.

The distinctive resistance characteristics of the lettuce cultivar 79-22 RZ seeds and plants of the present invention provides a significant advantage for growers trying to grow lettuce with many uniformly-sized leaves without the attendant high costs due to *Bremia* attacks. *Bremia* resistance prevents the "Socrates" plant from getting infected by downy mildew—the most prevalent disease of lettuce. Due to the *Bremia* resistance of the "Socrates" plant, the need for a number of costly fungicidial sprays is reduced.

This has the advantage of alleviating consumers' concerns about fungicide residues on their lettuce due to the reduction or absence of fungicide applications on the lettuce crops. Additionally, the *Bremia* resistance provided by the "Socrates" seeds and plants of the present invention decreases the number of harvest losses, resulting in a higher yield per unit area. Furthermore, the multileaf characteristic, i.e., extraordinary high number of leaves on a single lettuce plant, of the "Socrates" plant, provides the salad industry with a product that is very suitable for processing—after cutting the leaves from the main core of the lettuce head, no further sorting or cutting is required to produce an edible salad. This reduces the costs of bagged salad production and results in less labor and/or increased shelf life.

In the Tables that follow, the traits and characteristics of lettuce cultivar of "79-22 RZ", referred to as "Socrates", are given compared to a standard regional check variety, referred to as "Little Gem".

In Table 1, the seed color, cotyledon shape and characteristics of the fourth leaf of lettuce cultivar 79-22 RZ (Socrates) is compared with "Little Gem". The "Leaf Length/Width Index" is found by dividing the length by the width and multiplying by 10.

TABLE 1

| CHARACTER | SOCRATES | LITTLE GEM |
|---|---|---|
| Plant Type | Cutting/Leaf Type Lettuce | Bibb Type Lettuce |
| Seed Color | White (Silver Gray) | White (Silver Gray) |
| Cotyledon Shape | Broad | Broad |
| Cotyledon Shape of Fourth Leaf | No. 4 on FIG. 1 | No. 4 on FIG. 1 |
| Cotyledon Rolling of Fourth Leaf Stage | Absent | Absent |
| Cotyledon Cupping of Fourth Leaf Stage | Uncupped | Slight |
| Fourth Leaf Length/Width Index | 18 | 19 |
| Fourth Leaf Apical Margin | Crenate/Gnawed | Entire |
| Fourth Leaf Basal Margin | Moderately Dentate | Entire |
| Undulation | Flat | Flat |

In Table 2, the mature leaf and head characteristics of lettuce cultivar 79-22 RZ (Socrates) is compared with those of "Little Gem".

TABLE 2

| CHARACTER | SOCRATES | LITTLE GEM |
|---|---|---|
| Maturity (Earliness of Harvest-Mature Head Formation (Spring season) | 52 days | 52 days |
| Green Color | Light Green | Medium Green |
| Anthocyanin Distribution | Absent | Absent |
| Margin Incision Depth | Absent/Shallow | Absent/Shallow |
| Margin Indentation | Entire | Entire |
| Undulations of the Apical Margin | Absent/Slight | Absent/Slight |
| Leaf Size | Small | Small |
| Leaf Glossiness | Moderate | Moderate |
| Leaf Blistering | Absent/Slight | Strong |
| Leaf Thickness | Thin | Intermediate |
| Trichomes | Present (Spiny) | Absent (Smooth) |
| Spread of Frame Leaves | 24 cm | 28 cm |
| Head Diameter | 20 cm | 16 cm |
| Head Shape | Flattened | Spherical |
| Head Size | Small | Small |
| Head Weight | 356 g | 491 g |
| Head Firmness | Moderate | Firm |
| Butt Shape | Rounded | Rounded |
| Midrib | Moderately Raised | Moderately Raised |

In Table 3, the characteristics of the core and the bolter plant of lettuce cultivar 79-22 RZ (Socrates) is compared with those of "Little Gem".

TABLE 3

| CHARACTER | SOCRATES | LITTLE GEM |
|---|---|---|
| Core Diameter at Base of Head | 32 mm | 35 mm |
| Ratio of Head Diameter/Core Diameter | 6.3 | 4.6 |
| Core Height from Base of Head to Apex | 40 mm | 68 mm |
| Number of Days from first water date to seed stalk emergence | 101 | 86 |
| Bolting Class | Very Slow | Slow |
| Height of Mature Seed Stalk | 45 cm | 125 cm |
| Spread of Bolter Plant | 20 cm | 30 cm |
| Bolter Leaves | Straight | Curved |
| Margin | Dentate | Dentate |
| Color | Medium Green | Dark Green |
| Terminal Inflorescence | Absent | Absent |
| Lateral Shoots | Abent | Present |
| Basal Side Shoots | Present | Present |

While the invention has been particularly shown and described with reference to preferred embodiments thereof, it will be understood by those skilled in the art that various alterations in form and detail may be made therein without departing from the spirit and scope of the invention.

The invention claimed is:

1. A F1 or self progeny of a lettuce plant designated 79-22 RZ referred to as Socrates, representative seed of which having been deposited under NCIMB Accession No. 41325, wherein said progeny plant has genetic information for resistance to downy mildew (*Bremia lactucae* Regal) and an extraordinary high number of green, round-shaped leaves.

2. The progeny as claimed in claim 1, wherein said progeny plant has genetic information for and expresses resistance to downy mildew (*Bremia lactucae* Regal) and an extraordinary high number of green, round-shaped leaves, wherein the resistance to downy mildew (*Bremia lactucae* Regal) and an extraordinary high number of green, round-shaped leaves is as found in a lettuce plant, representative seed of which was deposited under NCIMB accession number 41325.

3. The progeny as claimed in claim 1, wherein said progeny is produced by sexual or vegetative reproduction.

4. The progeny as claimed in claim 2, wherein said progeny is produced by sexual or vegetative reproduction.

5. The progeny of claim 1 having all of the morphological and physiological characteristics of a lettuce plant, representative seed of which having been deposited under NCIMB Accession No. 41325.

6. The progeny of claim 2 having all of the morphological and physiological characteristics of a lettuce plant, representative seed of which having been deposited under NCIMB Accession No. 41325.

7. A seed of the plant of any one of claims 2-6, wherein a plant grown from said seed produces a lettuce plant designated 79-22 RZ referred to as Socrates, representative seed of which having been deposited under NCIMB Accession No. 41325, wherein said plant has genetic information for resistance to downy mildew (*Bremia lactucae* Regal) and an extraordinary high number of green, round-shaped leaves.

8. A part of the plant of any one of claims 2-6, wherein said part of the plant is suitable for vegetative reproduction and the part of the plant is a cutting, roots, stem, cell, protoplast, leaf, meristem or bud.

9. A tissue culture of the lettuce plant of any one of claims 1-6 wherein said tissue culture is derived from a tissue comprising a leaf, cotyledon, hypocotyl, meristematic cell, root, root tip, anther, flower, or stem.

10. The seed of the plant of any one of claims 2-6 which is seed having been deposited under NCIMB Accession No. 41325.

11. A plant grown from the seed as claimed in claim 7.

12. A plant regenerated from the part of the plant as claimed in claim 8.

13. A plant regenerated from the tissue culture as claimed in claim 9.

14. A method of producing a lettuce plant, or part thereof, having resistance to downy mildew (*Bremia lactucae* Regal) and an extraordinary high number of green, round-shaped leaves, comprising producing progeny from a lettuce plant of claim 1; wherein said progeny has resistance to downy mildew (*Bremia lactucae* Regal) and an extraordinary high number of green, round-shaped leaves.

15. A method of producing a lettuce plant, or part thereof, having genetic information for resistance to downy mildew (*Bremia lactucae* Regal) and an extraordinary high number of green, round-shaped leaves, comprising producing progeny from a lettuce plant of claim 1; wherein said progeny has genetic information for resistance to downy mildew (*Bremia lactucae* Regal) and an extraordinary high number of green, round-shaped leaves.

16. A method of producing a lettuce plant, or part thereof, having resistance to downy mildew (*Bremia lactucae* Regal) and an extraordinary high number of green, round-shaped leaves, comprising producing a progeny lettuce plant so having said resistance to downy mildew (*Bremia lactucae* Regal) and an extraordinary high number of green, round-shaped leaves, wherein said progeny lettuce plant is descended from a lettuce plant designated 79-22 RZ, having resistance to downy mildew (*Bremia lactucae* Regal) and an extraordinary high number of green, round-shaped leaves, representative seed of which having been deposited under NCIMB Accession No. 41325.

* * * * *